United States Patent [19]

Lilienfeld

[11] Patent Number: 4,940,327

[45] Date of Patent: Jul. 10, 1990

[54] METHOD AND APPARATUS FOR REAL TIME ASBESTOS AEROSOL MONITORING

[75] Inventor: Pedro Lilienfeld, Lexington, Mass.

[73] Assignee: TRC Companies Inc., East Hartford, Conn.

[21] Appl. No.: 262,457

[22] Filed: Oct. 25, 1988

[51] Int. Cl.⁵ ............................................. G01N 21/53
[52] U.S. Cl. ..................................................... 356/338
[58] Field of Search ................................ 356/338, 339

[56] References Cited

U.S. PATENT DOCUMENTS 3,692,412 9/1972 Chubb ................................ 356/338

OTHER PUBLICATIONS

"Rotational Electrodynamics of Airborne Fibers", Lilienfeld, J. Aerosol. Sci., vol. 16, No. 4, pp. 315-322, (1985).
"Light Scattering from Oscillating Fibers at Normal Incidence", Lilienfeld, J. Aerosol. Sci., vol. 18, No. 4, pp. 389-400, (1987).
"Alignment of Respirable Asbestos Fibers by Magnetic Fields", Timbrell, Ann. Occup. Hyg., vol. 18, p. 299, (1975).
"Rapid Screening for Detection of Asbestos Fibers in Water Samples", Chatfield and Riis, EPA-600/4-8-3-041, Sep. 1983.
MIE Fibrous Aerosol Monitor, Model FAM-1 User's Manual, MIE, Inc., 213 Burlington Road, Bedford, Mass. 01730, Aug. 1988.
Diagram entitled "FAM-1 Optics-Flow Diagram".
Diagram entitled "Optical Configuration of Fibrous Aerosol Monitor".
Diagram entitled "Quadrupole electric field configuration and optical detection geometry of GCA Fibrous Aerosol Monitor model FAM-1".

*Primary Examiner*—Davis L. Willis
*Assistant Examiner*—Matthew W. Koren
*Attorney, Agent, or Firm*—Morgan & Finnegan

[57] ABSTRACT

A real time asbestos aerosol monitor and method are provided. An ambient air sample is passed through a first sensing zone where fibers in the sample are electrically aligned and oscillated as they are illuminated perpendicular to the fiber axes with high intensity laser light. The scattered light signal pulse train from a first detector is analyzed to determine the presence and size of fibers in the sample. The air sample is then passed through a second sensing zone including a hybrid electric/magnetic field to electrically align and magnetically oscillate asbestos fibers. The sample in the second sensing zone is illuminated perpendicular to the fiber axes, with the scattered light signal pulse train from a second detector being analyzed to determine whether each fiber detected in the first sensing zone is an asbestos fiber. Advantageously, clean air is circulated across illumination optical surfaces to protect against abrasive elements in the air sample. Zeroing and calibration are also provided.

34 Claims, 5 Drawing Sheets

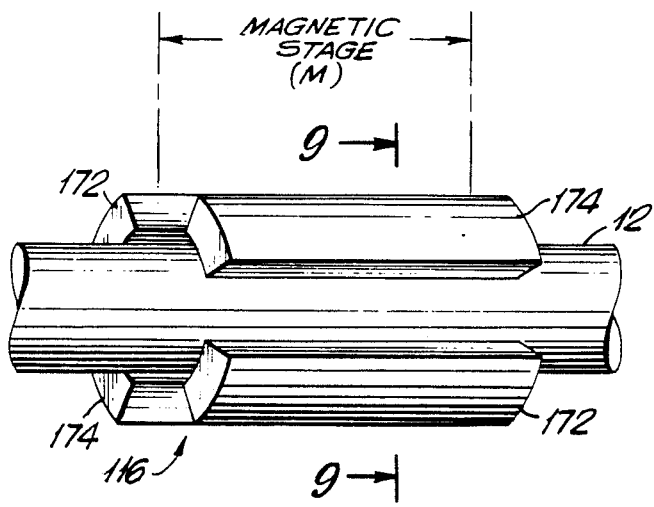
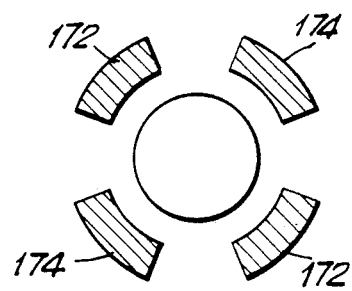
FIG.8  FIG.9
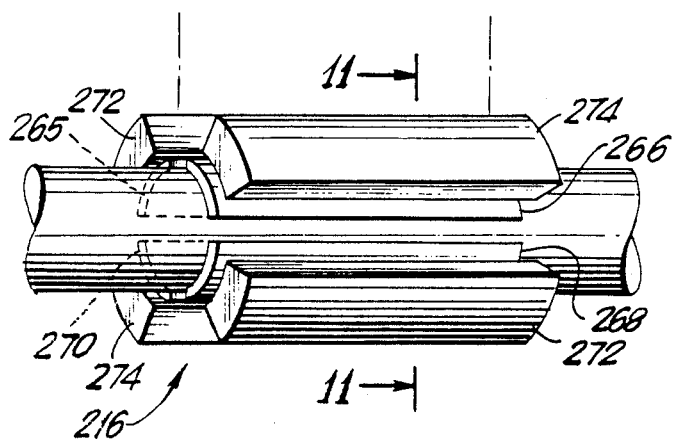
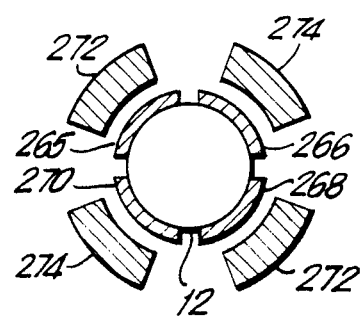
FIG.10  FIG.11

METHOD AND APPARATUS FOR REAL TIME ASBESTOS AEROSOL MONITORING

TECHNICAL FIELD

The present invention relates to an asbestos aerosol monitor and, more specifically, to a real time fibrous aerosol monitor capable of identifying and counting asbestos fibers.

BACKGROUND AND OBJECTS OF THE INVENTION

At present, standard methods for monitoring airborne asbestos fibers are based on filter sampling techniques. In such methods, asbestos fibers are collected on filter and are subsequently analyzed by optical or electron microscopy or chemical methods in order to determine asbestos concentration. These general methods suffer from several drawbacks, such as delayed availability of information, tediousness, inconvenience, high cost per sample, lack of precision, etc.

Although it is recognized that filter sample/microscopy techniques will most likely continue to be regarded as reference tools, there is a clearly established need for a real time asbestos monitor. This need is clearly demonstrated by the common practice of using the Fibrous Aerosol Monitor ("FAM-1") available from Monitoring Instruments for the Environment ("MIE"), Bedford, Massachusetts, for routine auxillary monitoring during and after asbestos removal and/or containment operations. The FAM-1 is a rugged and reliable field-worthy monitor capable of withstanding the rigors of asbestos removal operations. The FAM-1 samples the environment and simultaneously subjects the aerosol sample to constant and time-varying electric fields to align and oscillate the fibers while illuminating the fibers perpendicularly to their axes with polarized light. The pattern of light perpendicularly scattered by the aligned and oscillated fibers makes it possible for the FAM-1 to identify and count the number of fibers in the sample on a real time basis. The principles of operation of the FAM-1 to obtain fiber alignment and periodic oscillation are described in "Rotational Electrodynamics of Airborne Fibers", Lilienfeld, J. Aerosol Sci., Vol. 16, No. 4, pp. 315–322 (1985). The principles of operation of the FAM-1 optical system are illustrated and described in "Light Scattering From Oscillating Fibers At Normal Incidence", Lilienfeld, J. Aerosol Sci., Vol. 18, No. 4, pp. 389–400 (1987).

The FAM-1, however, is incapable of distinguishing asbestos fibers from other types of fibers, e.g. glass, polymer, cellulose, textile, etc. In addition, the FAM-1 is only capable of detecting fibers longer than 2 micrometers with diameters as small as 0.1 micrometers, whereas current Environmental Protection Agency ("EPA") requirements call for detection of fibers as short as 0.5 micrometers with diameters less than 0.1 micrometers. To date, however, the FAM-1 provides the only practical real time aerosol monitor for auxillary asbestos fiber monitoring.

Therefore, it is one object of the present invention to provide a real time asbestos monitor.

Another object of the invention is to provide a real time asbestos aerosol monitor capable of identifying asbestos fibers and distinguishing such asbestos fibers from other types of fibers.

Yet another object of the present invention is to provide a real time asbestos monitor capable of identifying and counting asbestos fibers as short as 0.5 micrometers with diameters less than 0.1 micrometers.

These and other highly desirable and unusual results are accomplished by the present invention in a compact, portable real time asbestos aerosol monitor capable of identifying asbestos fibers and distinguishing asbestos fibers from other types of fibers for counting.

Objects and advantages of the invention are set forth in part herein and in part will be obvious herefrom, or may be learned by practice with the invention, the same being realized and attained by means of the instrumentalities and combinations pointed out in the appended claims.

The invention consists of the novel parts, constructions, arrangements combinations, steps and improvements herein shown and described.

SUMMARY OF THE INVENTION

The preferred embodiment in accordance with the present invention provides a real time asbestos aerosol monitor having an aerosol sampling and flow control system, an electric sensing field, a hybrid electric/magnetic sensing field, a high intensity illumination system for illuminating the fibers perpendicular to the fiber axes, and scattered light detectors oriented perpendicular to the direction of illumination to detect light reflected from the fibers.

In the preferred embodiment, the aerosol sampling and flow control system consists of a sensing flow tube which receives air sampled from the environment. Preferably, the sampled air is passed through a virtual impactor to eliminate the larger than inhalable or respirable fiber fraction and neutralized in an electrical charge neutralizer prior to being introduced to the sensing tube. Preferably, the sample stream enters the flow sensing tube through an angled feed pipe to reduce particle loss due to wall collisions. The air sample travels through the flow sensing tube, including the first, electric field sensing stage and the second, hybrid electric/magnetic field sensing stage before exiting the sensing flow tube through a constant suction side duct connected to a filter and a vacuum source. The vacuum source may be an air pump and pulsation dampener. Preferably, the distance travelled by the sample stream within the flow tube from its inlet to the first sensing stage is sufficiently long to ensure constant laminar flow through the first and second sensing stages. The rate of flow of the vacuum pump exhaust is measured in order to monitor and control sample velocity within the sensing flow tube.

The first, electric field at the first sensing stage consists of a high voltage d.c. field to vertically align the fibers and a time varying a.c. electric field to induce time-dependent oscillation of fibers contained within the sample.

The second, hybrid electric/magnetic field at the second sensing stage consists of a high voltage d.c. electric field to vertically align all fibers in the sample, and a time-varying magnetic field to induce time-dependent oscillation of asbestos fibers only. Non-asbestos fibers are not affected by the magnetic field and remain in vertical alignment in the second sensing stage.

The high intensity illumination beam preferably consists of an expanded, vertically polarized beam from an intracavity helium-neon or other gas laser oriented on the axis of the flow tube, and illuminates fibers vertically aligned in the first and second sensing stages perpendicular to the fiber axes. To obtain more uniform fiber illumination and enhance sensitivity, the intracavity laser beam is reflected back from a mirror disposed at the opposite end of the flow tube, thereby obtaining very high intensity bilateral illumination perpendicular to the axes of the vertically aligned fibers.

A first, electric field detector provided with a field of view slit aperture and polarizing filter receives light scattered from vertically aligned fibers disposed along the flow tube axis within the first sensing stage. As fibers disposed in the first, electric field oscillate from a vertical alignment under the influence of the time-varying a.c. electric field, an identifiable light scattering signature develops and may be analyzed to determine the presence, length, diameter, etc. of fibers in the sample. High intensity illumination and selection of the field of view aperture permit detection of fibers at least as small as 0.5 micrometers in length and less than 0.1 micrometers in diameter.

A second, magnetic field detector, also provided with a field of view slit aperture and a polarizing filter, views the axial portion of the sample passing through the hybrid electric/magnetic field. The second detector receives and detects light scattered from all fibers vertically aligned by the d.c. electric field. Significantly, however, a scattered light signal indicative of the presence of asbestos fibers is developed as asbestos fibers are induced to oscillate in the time-varying magnetic field introduced at the second sensing stage.

The elapsed time between detection of a fiber at each sensing stage is readily determined from the distance between sensing stages and the velocity of fibers along the axis of the sensing flow tube, permitting correlation of the scattered light signal patterns for a fiber at both sensing stages.

The asbestos monitor determines whether a fiber has been detected based on the frequency, phase and pulse shape of the signal at the first sensing stage. Pulse amplitude and area are used to determine fiber length and diameter. The corresponding frequency, phase and pulse shape for the same sample portion at the second sensing stage indicate whether the fiber is asbestos material responsive to a magnetic field. Where the corresponding first and second sensing stage signals indicate the presence of a fiber responsive to a magnetic field, the monitor concludes that the fiber is asbestos and counts the fiber as an asbestos fiber. Given the known volume flow of the sample the number of asbestos fibers counted per unit time corresponds to asbestos fiber concentration and may be converted to units of fibers per cubic centimeter.

Advantageously, a small portion of the clean exhaust air flow is directed across the optical illumination surfaces at either end of the flow tube, i.e. the laser window or a beam expander and the reflective mirror, to protect those surfaces.

In a zeroing and calibration procedure, the main exhaust is closed so that the atmosphere is not sampled and only clean, filtered air is circulated through the sensing flow tube. A zero reading is taken and calibration LED's are activated to simulate scattered light sensing signals corresponding to asbestos fiber detection.

Thus, the present invention provides, for the first time, an aerosol monitor capable of distinguishing and counting asbestos fibers to determine asbestos concentration on a real time basis. Advantageously, high intensity polarized laser illumination permits detection and calculation of fiber dimensions within current EPA requirements. As a further advantage of the present invention, optical surfaces are protected from contact with sample air containing abrasive particles and fibers. Zeroing and calibration are also provided. Surprisingly, the foregoing highly desirable results are accomplished in a compact and rugged portable asbestos aerosol monitor.

It will be understood that the foregoing general description and the following detailed description as well are exemplary and explanatory of the invention but are not restrictive thereof.

BRIEF DESCRIPTION OF THE DRAWINGS

The accompanying drawings, referred to herein and constituting a part hereof, illustrate preferred embodiments of the product of the present invention, and together with the description serve to explain the principles of the invention.

FIG. 8 is a partial perspective view of a sensing stage in accordance with a first alternative embodiment of the invention;

FIG. 9 is a cross section view of the sensing stage illustrated in FIG. 8, taken along lines 9—9 of FIG. 8;

FIG. 10 is a partial perspective view of a sensing stage in accordance with a second alternative embodiment of the invention; and FIG. 11 is a cross-section view of the sensing stage illustrated in FIG. 10, taken along lines 11—11 of FIG. 10.

DETAILED DESCRIPTION OF THE PREFERRED EMBODIMENTS

Figure 1:
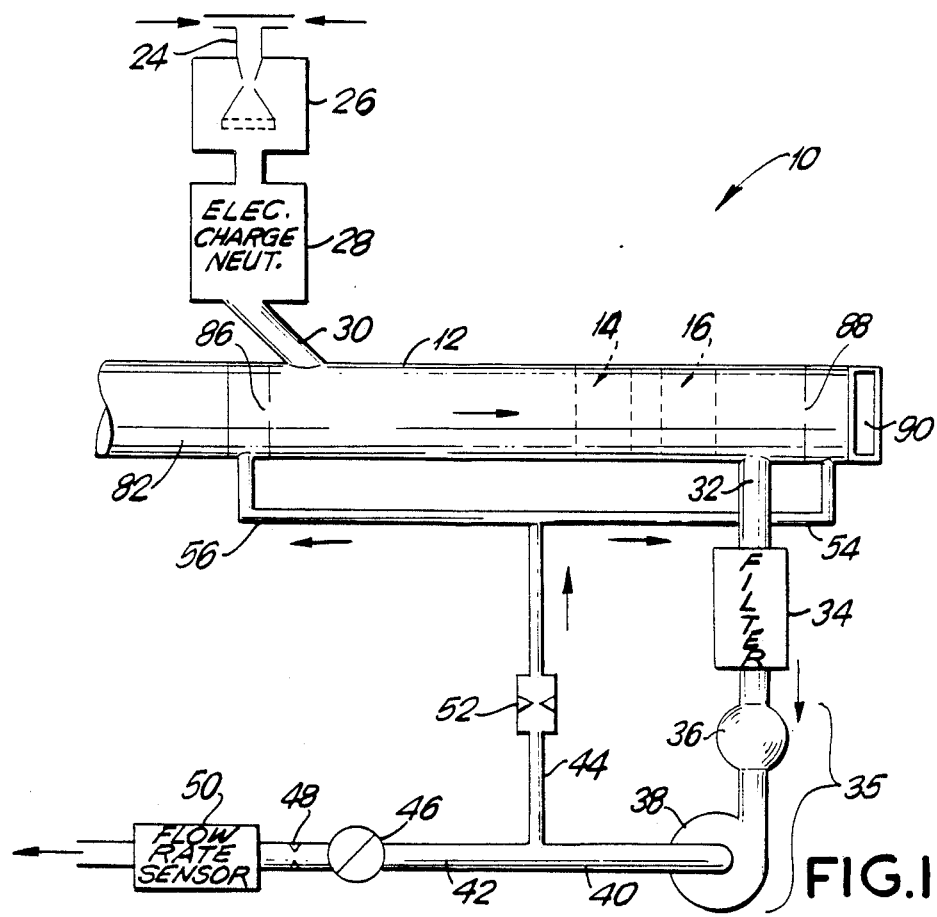
FIG. 1 is a partial schematic view of the aerosol sampling and flow system utilized in the present invention.

Referring now to the drawings, there is shown an asbestos aerosol monitor 10 for sampling the ambient atmosphere. The air sample is injected into a flow tube 12 and traverses the flow tube from left to right through a first, electric field 14 and, subsequently, through a second, hybrid electric/magnetic field 16. During the first, electric field stage the sample is illuminated with light from a high intensity light source 18 (see FIG. 5), and light scattered from fibers within the air sample is detected by a first scattering detector 20. While traveling through the hybrid electric/magnetic field 16, the air sample is again illuminated with light from high intensity light source 18 and light scattered from fibers in the sample is detected by a second scattering detector 22. The response of the first scattered light detector is indicative of the presence of fibrous material in the sample. The response of the second scattered light detector is indicative of the presence of asbestos in the sample. The volume and rate of flow of the air sample through flow tube 12 are used to correlate the first and second stage analysis results to provide a real time measure of the concentration of asbestos fibers within a specific size range.

Referring more specifically to FIG. 1, there is shown a general schematic view of the preferred flow system in accordance with the invention for obtaining representative sampling of the environment with fully developed, constant laminar flow conditions at the first and second sensing stages As shown in FIG. 1, an air sample is obtained through a sampling inlet 24, preferably an omnidirectional slit-type entry port. Depending upon sampling requirements, other types of inlets, such as a straight pipe inlet, may be appropriate. Inlet 24 is preferably followed by a single stage virtual impactor 26 designed to capture the larger than 10 micrometer particle size fraction, which is considered non-inhalable and outside the scope of current EPA test requirements. Other particle size segregation values may also be considered. The preferred embodiment also includes an electrical charge neutralizer 28, such as an electrical charge neutralization stage containing a Kr-85 radioactive source. A feed pipe 30 connects neutralization stage 28 to flow tube 12, so that the neutralized air sample is fed through feed pipe 30 to flow tube 12. Feed pipe 30 is preferably angled relative to flow tube 12, such as at a 45° angle, in order to minimize particle losses due to wall impaction. A sufficient distance, such as ten flow tube diameters, is provided between feed pipe 30 and the first sensing stage 14 to ensure stable laminar flow during sensing in the two consecutive electric and hybrid electric/magnetic sensing stages 14, 16. A side duct 32 is connected to flow tube 12 downstream from sensing stages 14, 16. Side duct 32 leads to an in-line membrane filter 34 connected to a vacuum system 35. The vacuum system may consist of a pulsation dampener 36 connected to an air pump 38 operating at approximately 5 liters per minute. Of course, it is contemplated that filter 34 may be analyzed by standard chemical and/or microscopic methods to confirm the real time asbestos fiber count obtained with the present invention. As shown, the pump exhaust 40 is split into a main exhaust branch 42 and a secondary exhaust branch 44. Main branch 42 includes a solenoid valve 46, a main branch flow resistance element 48, and a flow rate sensor 50. The secondary exhaust branch 44 includes a secondary flow resistance member 52 and two clean air return pipes 54, 56 connected near the distal ends of flow tube 12. Preferably, flow tube 12 has a diameter of 1 to 2 cm, resulting in an on axis fiber velocity of about 200 to 50 cm/sec.

Figure 2:
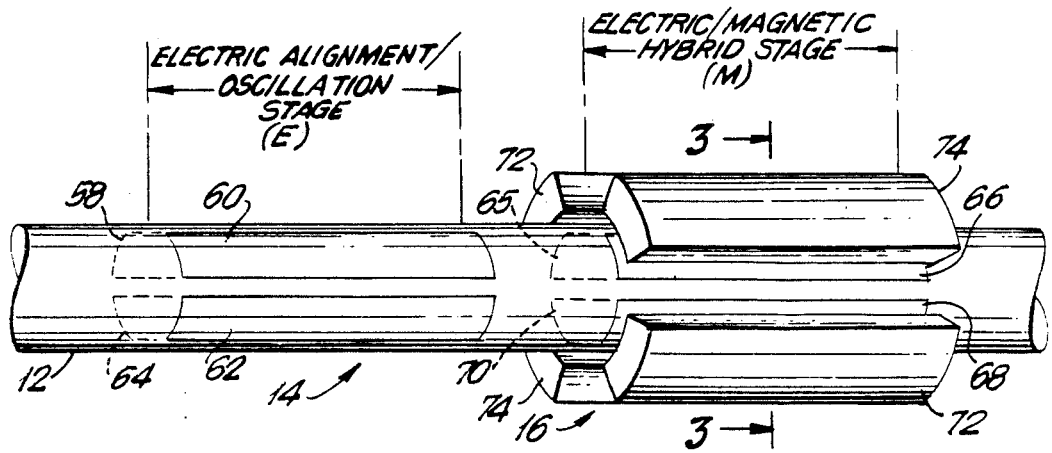
FIG. 2 is a partial perspective view of the first and second sensing stages in accordance with the invention.
Figure 3:
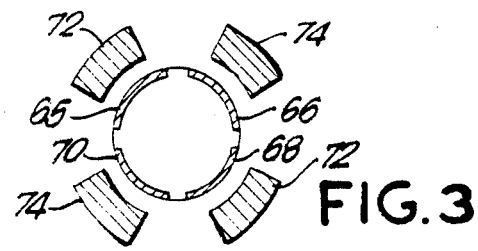
FIG. 3 is a cross-section view of the second sensing stage, taken along lines 3—3 of FIG. 2.

Fiber alignment and oscillation in each of the sensing stages 14, 16 may be described with reference to FIGS. 2 and 3. As shown in FIG. 2, sensing stage 14 includes an electric field quadrupole for aligning and oscillating all fibers in the specimen for detection. This type of time varying electric field quadrupole is illustrated and described in "Rotational Electrodynamics of Airborne Fibers", Lilienfeld, J. Aerosol Sci., Vol. 16, No. 4, p. 315 at pp. 319–321 (1985). In general, four quadrupole elements 58, 60, 62, 64 (58 and 64 shown in phantom) are provided and a high voltage d.c. field is applied across the a left side quadrupole member pair 58, 64 and a right side quadrupole member pair 60, 62 to vertically align the fibers in the stream. An a.c. voltage is applied across the upper quadrupole member pair 58, 60 and the lower quadrupole member pair 62, 64. The superimposed fields result in a field intensity at the center of the quadrupole of between 3,000 to 3,400 volts per centimeter, with fibers in the field aligned vertically when the a.c. component passes through zero. As the a.c. component increases in the positive or negative direction, fibers in the sample are rotated out of vertical alignment and periodically oscillate. Because light scattered from perpendicularly illuminated fibers is sharply concentrated at and near the plane normal to the fiber axis, the foregoing electric field, as included in the FAM-1 available from MIE, makes it possible to observe and count the concentration of fibers present in a given sample. See "Light Scattering From Oscillating Fibers At Normal Incidence", Lilienfeld, J. Aerosol Sci., Vol. 18, No. 4, p. 389 (1987).

Although the first, electric field desirably permits identification of fibers and calculation of their size and concentration, the electric field sensing stage is incapable of distinguishing asbestos from other types of fibers. In other words, substantially all types of fibers, including glass, polymer, textile and cellulose fibers, behave similarly in the electric field and cannot be distinguished from asbestos fibers.

However, it has been observed that asbestos fibers have a unique property not found in other types of fibers: paramagnetism. The behavior of asbestos fibers in a magnetic field is reported in "Alignment of Respirable Asbestos Fibers by Magnetic Fields", Timbrell, Ann. Occup. Hyg., Vol. 18, p. 299 (1975). As distinguished from glass fibers, polymer fibers, fibers of organic origin, and most types of chain aggregates (with the exception of ferro-metallic fume agglomerates), asbestos fibers are aligned when exposed to a magnetic field. Magnetic field-induced asbestos fiber alignment occurs in two orthogonal directions: either parallel ("P-fibers") or normal ("N-fibers") to the magnetic field lines. The experiments described by Timbrell indicate that, in the majority of cases, all fibers from a given sample tend to align along one of the two axes, although certain types of asbestos may exhibit both types of alignment. Typically, Timbrell found that UICC anthophyllite from Finland exhibits P-alignment and India amosite consists of N-fibers, whereas UICC amosite from Transvall (South Africa) consists of both P-fibers and N-fibers. Table 1 summarizes Timbrell's observations.

TABLE 1

Alignment modes of Asbestos Fibers in a Magnetic field

| Types of asbestos | Source of sample | Alignment Mode |
| --- | --- | --- |
| 1. Anthophyllite (UICC) | Finland | P |
| 2. Amosite | India | N |
| 3. Amosite (UICC) | Transvaal (S. Africa) | P and N |
| 4. Crocidolite (UICC) | Cape Province (S. Africa) | P |
| 5. Tremolite | Uganda | P |
| 6. Tremolite | Zululand | N |
| 7. Chrysotile | Canada | P |

It is interesting to note that of the samples studied by Timbrell only South African amosite exhibited a mixture of P and N-type fibers, all others were of one type or of the other but did not contain both concurrently. The magnetic field intensity required to align asbestos fibers in water was found to be of the order of 3 K gauss (0.3 tesla). Similar results were reported by Chatfield and Riis, although these investigators found that chrysotile fibers required a higher field intensity (0.4 T) than other types of asbestos to achieve complete alignment in a water suspension. See "Rapid Screening for Detection of Asbestos Fibers in Water Samples", Chatfield and Riis, EPA-600/4-83-041, September, 1983.

The second sensing stage of the asbestos monitor according to the present invention takes advantage of the unique paramagnetism of asbestos fibers in order to positively identify such fibers. In second sensing stage 16 a hybrid electric/magnetic field is created wherein an electric quadrupole is provided having electric quadrupole elements 65, 66, 68, 70 (65, 70 shown in phantom). A time-varying electromagnetic field is also created using electromagnets 72, 74 (see FIG. 3). In this fiber alignment and oscillation stage, a d.c. field is applied across left and right electric quadrupole element pairs 65, 70 and 66, 68, respectively, to create a d.c. field intensity between 3,000 to 4,000 volts per centimeter. As in the case of the d.c. field in the first alignment and oscillation stage, this electric field obtains vertical alignment of all fibers in the sample, including both asbestos and non-asbestos varieties, to within a small fraction of a degree.

The time-dependent magnetic field is created by applying a half-wave sinusoidal voltage to each electromagnet 72, 74. Each sinusoid is 90° out of phase so that, as the magnetic field intensity of one electromagnet peaks, the magnetic field intensity of the other electromagnet is zero. Similarly, as the magnetic field of one electromagnet decreases to zero the field of the other electromagnet begins to increase.

Figure 4A:
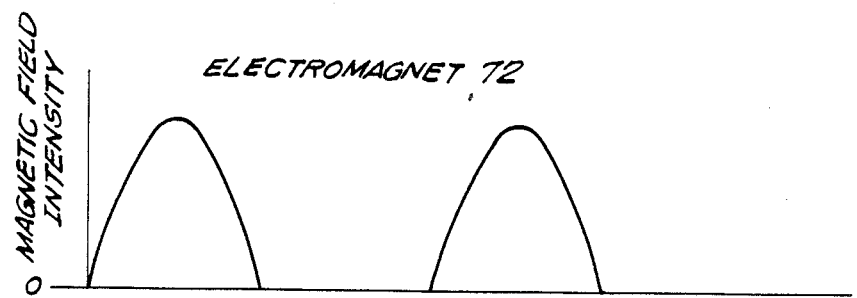
FIG. 4A is a graphic illustration of the time-varying magnetic field created at the second sensing stage by a first electromagnet.
Figure 4B:
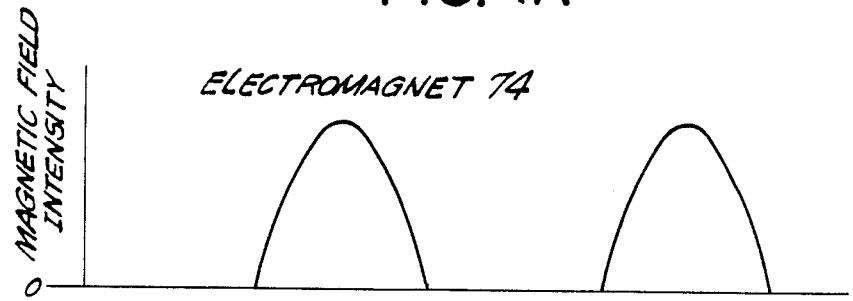
FIG. 4B is a graphic illustration of the time-varying magnetic field created at the second sensing stage by a second electromagnet.
Figure 4C:
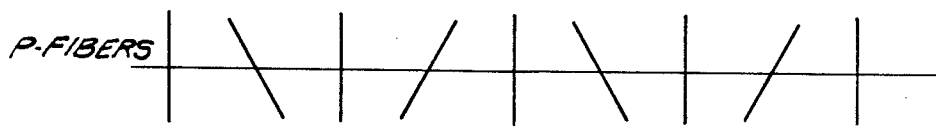
FIG. 4C is a graphic illustration of the effects of the magnetic fields illustrated in FIGS. 4A and 4B on a vertically aligned P-type asbestos fiber.
Figure 4D:
FIG. 4D is a graphic illustration of the effects of the magnetic fields illustrated in FIGS. 4A and 4B on a vertically aligned N-type asbestos fiber.

The effects of the time-varying magnetic field upon asbestos fibers and the resulting light scattering signals are shown in FIGS. 4A through 4E. FIG. 4A illustrates the magnetic field intensity resulting over time from the half-wave sinusoidal voltage applied to electromagnet 72. Similarly, FIG. 4B shows the corresponding time-dependent magnetic field intensity resulting from the half-wave sinusoidal voltage applied to electromagnet 74. As shown, when one electromagnetic field has positive intensity the other field has zero intensity. FIGS. 4C and 4D illustrate the positional effect of each magnetic field condition on each type of vertically aligned asbestos fiber. When electromagnet 72 is activated, as shown by a positive magnetic field intensity in FIG. 4A, electromagnet 74 has zero magnetic field intensity and asbestos fibers are deflected from the vertical position induced by the electric field. As shown in FIGS. 4C and 4D, P-type asbestos fibers respond to a given magnetic field by deflecting in one rotational direction while N-type fibers respond to the same magnetic field by deflecting substantially the same amount in the opposite direction. Where both magnetic fields have zero intensity, i.e. where the half-wave sinusoidal voltage applied to one electromagnet reaches zero but the half-wave sinusoidal voltage applied to the other electromagnet has yet to increase above zero, asbestos fibers of either type are acted upon only by the d.c. electric field component of the hybrid electric/magnetic field and remain in vertical alignment. The alternating magnetic deflection fields coupled with the d.c. electric field results in a rhythmic, periodic oscillation of asbestos fibers around the vertical equilibrium alignment position determined by the d.c. electric field. Non-asbestos fibers are not affected by the time-varying magnetic field.

Figure 4E:
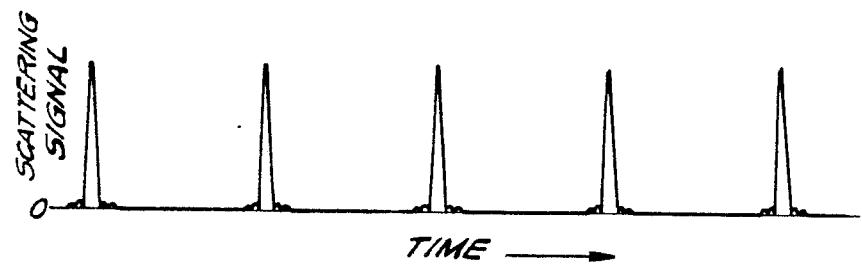
FIG. 4E is an illustration of the light scattering signal corresponding to the fiber positions illustrated in FIGS. 4C and 4D.

The effects of the electric/magnetic alignment and oscillation of asbestos fibers on the light scattering signal detected by detector 22 (see FIG. 5) are illustrated in FIG. 4E. When the asbestos fibers are subjected only to the d.c. electric field, i.e. when no voltage is applied to either electromagnet, light scattered from the perpendicularly illuminated fibers is highly concentrated at detector 22 to provide a high peak response As the fiber is subjected to an electromagnetic field and rotates out of vertical alignment, however, light scattered from the fiber and incident on detector 22 falls off dramatically. Advantageously, the scattered light signal is the same for either type of asbestos fiber and the asbestos fiber monitor according to the invention detects either type of fiber.

The peak, or maximum intensity of the varying magnetic field will depend on the maximum required angular deflection to be imparted to the asbestos fibers as they oscillate about the vertical alignment position. This angle of deflection depends on the vectorial addition of the forces resulting from the two fields, electric and magnetic, acting on the asbestos fibers. It is contemplated that the electric and magnetic fields might be oriented at 45° with respect to each other, as illustrated herein. It is estimated that the required peak intensity of the magnetic field will be of the order of 0.1 to 0.2 tesla. The magnetic torque on the fibers will, however, depend also on the magnetic susceptibility of each fiber which, in turn, will depend on fiber composition and crystalline morphology. For example, it is likely that for the same peak amplitude of the applied magnetic field, the angle of deflection of asbestos fibers in the electric/magnetic field substage will vary depending on the type of asbestos; e.g. amosite fibers will be deflected more than chrysotile fibers. It is contemplated that the variation in deflection angle might be correlated to distinguish between types of asbestos fibers.

Because the hybrid electric/magnetic alignment and oscillation substage induces asbestos fiber oscillations whose angular amplitude is asbestos fiber-type dependent, the resulting light scattering signals will be ambiguous with respect to fiber length, the determination of which requires constant angular deflection. In the preferred embodiment of the invention including two sensing stages, the length and diameter of each passing fiber is determined in the electric field sensing stage 14 and the fiber type, i.e. asbestos or non-asbestos, is determined in the hybrid electric/magnetic field stage. To some extent, the type of asbestos fiber might also be determined based on degree of response to the magnetic field.

Figure 5:
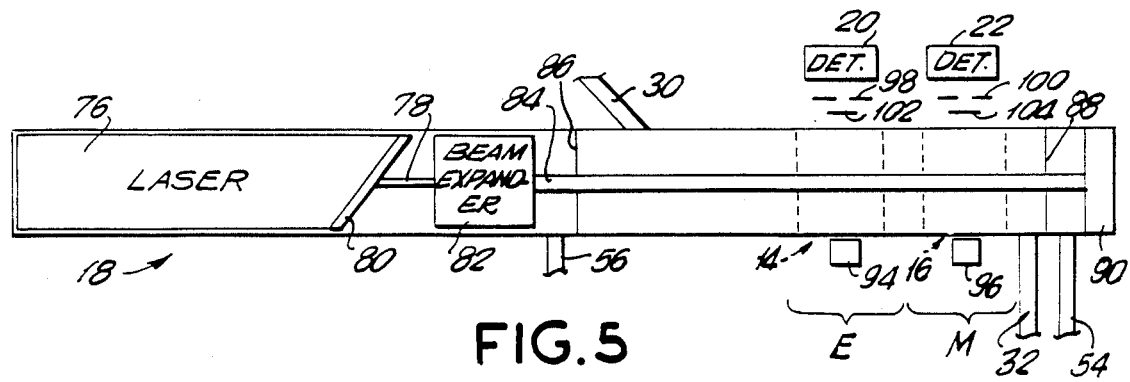
FIG. 5 is a schematic illustration of the illumination and scattered light detection system in accordance with the invention.

The illumination and scattered light sensing configuration of the present invention is best described with reference to FIG. 5. An intracavity laser 76 disposed within the flow tube emits a high intensity laser beam 78 through a Brewster angle window 80. Laser beam 78 may be expanded by a beam expander 82 to an expanded beam 84 aligned with the axis of flow tube 12. The on-axis beam 84 passes through a first illumination aperture 86 and axially traverses flow tube 12 through sensing stages 14, 16, where a portion of the light beam is scattered by fibers in the sample stream. The remaining portion of beam 84 passes through a second illumination aperture 88 and is reflected by an external laser cavity mirror 90. The portion of beam 84 reflected from mirror 90 passes back through aperture 88 so that fibers in the first and second sensing stages are illuminated bilaterally from both sides perpendicular to the axes of the aligned fibers, thereby enhancing detected scatter signal uniformity. As shown, clean air pipe 54 enters flow tube 12 between second aperture 88 and external laser cavity mirror 90, and clean air pipe 56 enters flow tube 12 between first aperture 86 and beam expander 82. In this preferred arrangement, a constant supply of clean filtered air flows across and protects the beam expander and mirror surfaces. Preferably, laser 76 is a 25 helium-neon laser operating at its optimal wavelength of 632.8 nanometers, and beam expander 82 is a 3X beam expander. This intracavity laser illumination system achieves very high intensity illumination of the sample in the flow tube, greatly increasing sensitivity of the system so that very small fibers within current EPA standards may be detected and categorized.

Light scattered from vertically aligned fibers is incident on and detected by detectors 20, 22 corresponding to the first and second sensing stages, respectively. Detectors 20, 22 may be identical side-window photomultiplier detectors although other types of detectors, such as a charge coupled device ("CCD") linear array of detectors may be appropriate. The size and separation of CCD's in a linear array detector would be determined by the field oscillation frequency and the air flow velocity in the axial region of the sensing section. Preferably, the laser beam is vertically polarized and each detector is preceded by a field-of-view slit aperture 98, 100 and a polarizing analyzer 102, 104 oriented for transmission of the vertically polarized scattered light component. This preferred arrangement optimizes the signal-to-noise ratio and ensures that all detected fibers are illuminated with approximately equal light intensity. Field of view slit apertures 98, 100 advantageously restrict the radial field of view of each detector so that only fibers passing along the central portion of the laser beam will be detected. Pulsed LED calibrators 94, 96 are also provided for illuminating detectors 20, 22 for instrument calibration.

The corresponding scattered light detection signals at each of electric sensing stage 14 and hybrid electric/magnetic sensing stage 16 are used to determine (1) whether a fiber is detected and (2) whether the fiber is an asbestos fiber. The time delay $\Delta t$ between sensing of a particular fiber at each sensing location corresponds to the geometric offset distance between the two sensing stages divided by the sample stream velocity along the flow tube axis, i.e. along the laser beam. $\Delta t$ remains invariant for a constant air flow rate, and flow rate sensor 50 monitors the system flow rate (see FIG. 1).

Thus, for any given sample stream sequential, corresponding signal pulse trains are established at each sensing stage.

Figure 6A:
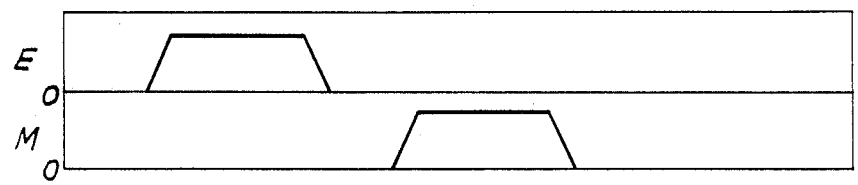
FIG. 6A is a graphic illustration of the scattered light signals corresponding to an essentially isotropic particle sample.
Figure 6B:
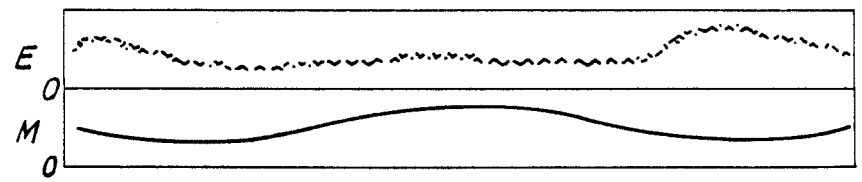
FIG. 6B is a graphic illustration of the scattered light signals corresponding to an irregular dust sample.
Figure 6C:
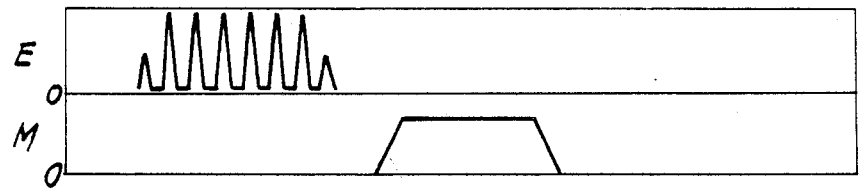
FIG. 6C is a graphic illustration of the scattered light signals corresponding to a non-asbestos fiber sample.
Figure 6D:
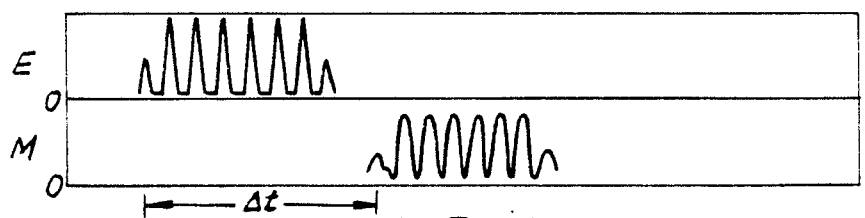
FIG. 6D is a graphic illustration of the scattered light signals corresponding to an asbestos fiber sample.

The manner by which the present system recognizes asbestos fibers is best described with reference to FIGS. 6A through 6D. In FIGS. 6A–6D the sequential signal pulse train for each of the electric "E" and magnetic "M" sensing stages is illustrated for different types of sampled material. In FIG. 6A, the signal pulse trains for a single essentially isotropic particle, i.e. a spherical droplet, salt crystal etc., are illustrated. As shown, the signal remains substantially constant during both signal pulses. In FIG. 6B, the random signal pulse trains for irregularly shaped dust particles are shown. FIG. 6C illustrates the signal pulse train for a single, non-asbestos fiber. Here, the periodic oscillating electric field pulse train shows that a fiber has been aligned by the d.c. field and periodically oscillated by the a.c. field to produce a signal pulse train characteristic of a fiber. In the magnetic field M, the non-asbestos fiber remains vertically aligned and is not oscillated, resulting in a substantially constant signal pulse similar to that obtained for an isotropic particle (compare FIG. 6A). Only where an asbestos fiber traverses both fields will corresponding periodic oscillating signal trains be obtained (see FIG. 6D). The electric field signal train confirms that the particle is a fiber and, due to the constant angular deflection of the electric field E, permits fiber length and diameter to be determined in a known manner. The magnetic field M causes periodic oscillation of asbestos fibers only, thereby providing positive identification of asbestos fibers regardless of the presence of other types of materials. The frequency of the pulses detected at each sensing stage is determined by the respective driving field frequencies for the electric field E and the magnetic field M. The two driving frequencies need not be identical but should be constant so as to permit synchronous phase-sensitive electronic signal processing.

During operation, vacuum system 35 provides constant suction through filter 34 and side duct 32 to flow tube 12, causing ambient air to be drawn through entry port 24, virtual impactor 26, electrical neutralizer 28, and feed pipe 30 into the flow tube. Entry port 24 and virtual impactor 26 ensure that the proper particle fraction, e.g. less than 10 micrometers, is drawn into the asbestos aerosol monitor. Charge neutralizer 28 advantageously neutralizes any electrical charge in the sample in order to ensure that the fibers remain at the same radial position within flow tube 12 during both sensing stages. Feed pipe 30 introduces the sample into the flow tube at an angle to reduce turbulence and particle loss due to wall impaction. The sample establishes stable laminar flow in flow sensing tube 12 prior to reaching sensing stages 14, 16, and enters the sensing stages in a uniform flow. During sensing, solenoid valve 46 is substantially open and only a small amount of the clean exhaust air, e.g. 5%, is diverted through clean air pipes 54, 56 to protect the illumination optics. The rate of flow of air through the system is sensed by flow rate sensor 50.

In electric field stage 14 all axial fibers are uniformly aligned and illuminated with light from high intensity expanded, polarized laser beam 84. Light scattered from the aligned and oscillated fibers at electric sensing stage 14 is detected by first detector 20 and is electronically analyzed to determine whether a signal pulse train indicative of the presence of fibers in the sampling stream is established.

After passing through the first electric sensing field 14 the sample stream passes through the combined electric and time-varying magnetic fields of sensing stage 16. As in the first sensing stage, the d.c. electric field vertically aligns all fibers in the sample. The time-varying magnetic field causes only asbestos fibers in the stream to periodically oscillate away from the vertical alignment induced by the electric field. Because only asbestos fibers are susceptible to magnetic oscillation, the variation in signal response at second detector 22 due to introduction of the magnetic field can be used to discern asbestos fibers from other types of fibers. Based upon the known dimensions of flow tube 12, the velocity of fibers from one sensing stage to the next and $\Delta t$ may be calculated, and the corresponding signal pulse trains for one sample portion can be correlated to compare behavior of a particular fiber in each sensing stage.

Figure 7:
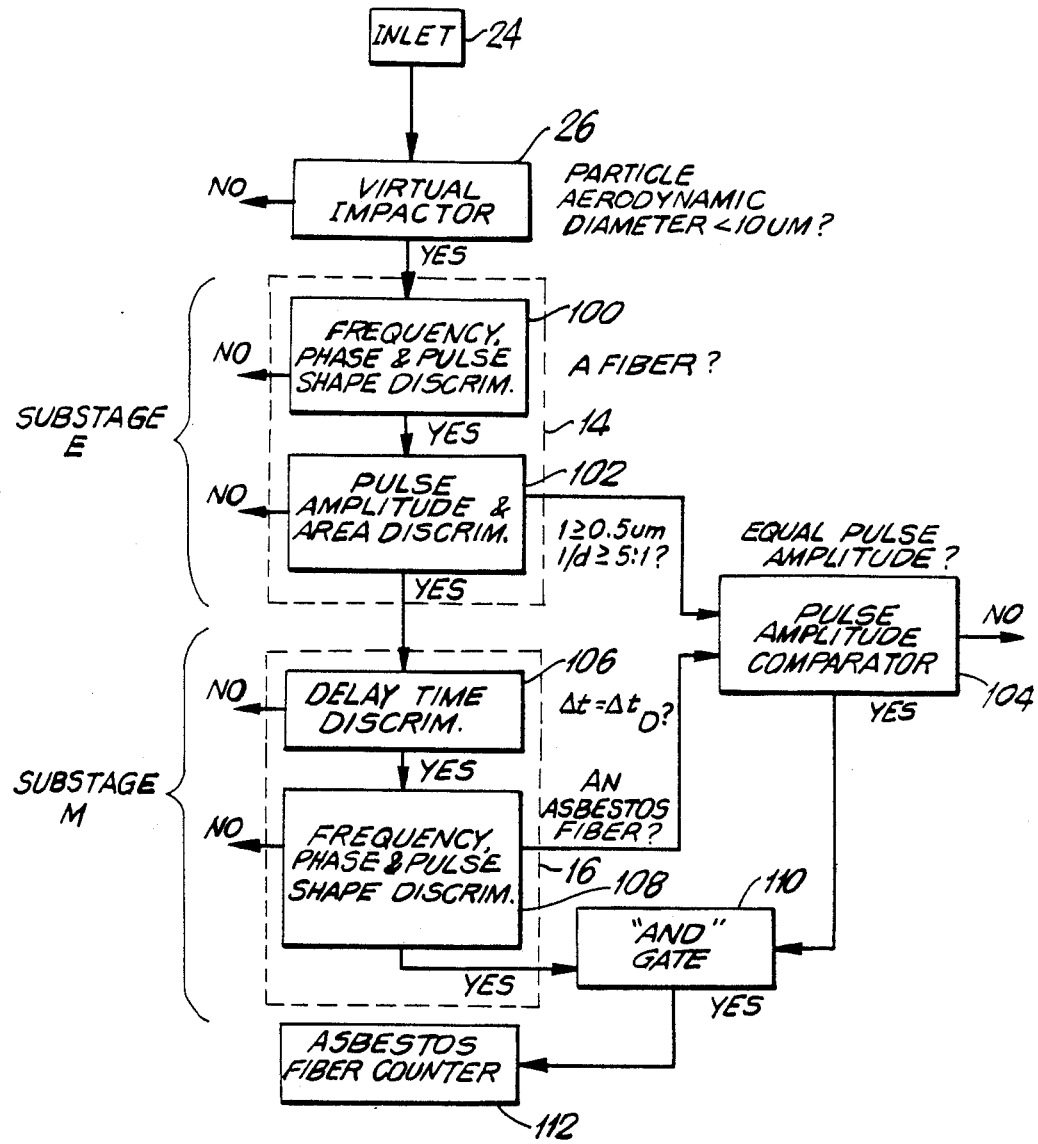
FIG. 7 is a block diagram illustration of the decision making process utilized in the present invention.

The logic system of the asbestos fiber monitor in accordance with the present invention is illustrated in the block diagram of FIG. 7. A sample enters through inlet 24 and passes through virtual impactor 26 to ensure that only the smaller particle fraction is introduced to sensing flow tube 12. As the sample stream is subjected to the electric field at first sensing stage 14, i.e. "Substage E", a first frequency phase and pulse shape discriminator 100 determines whether a fiber has been detected, i.e. by determining whether a periodic oscillating electric field signal train is present (see FIGS. 6C and 6D). A pulse amplitude and area discriminator 102 determines whether the fiber length is greater than or equal to the preset lower fiber length limit, preferably 0.5 microns, and whether the preset minimum aspect ratio of fiber length to diameter, preferably 5:1, is satisfied. Should either determination be negative, the apparatus determines that the material detected is not a fiber appropriate for consideration. If a fiber of requisite size is determined to have been detected, the pulse amplitude is transmitted to pulse comparator 104 and the apparatus proceeds to the second sensing stage 16. Where it is concluded either that a fiber has not been detected or that a fiber outside the requisite dimensional parameters has been detected, the system stops analyzing that portion of the sample and looks for a new sample portion containing a fiber of requisite dimensions.

A delay time discriminator 106 determines when the delay period equals $\Delta t$, indicating that the fiber detected at Substage E has entered the second sensing stage 16, i.e. "Substage M". A second frequency phase and pulse discriminator 108 determines whether a magnetic field signal train M has been detected which would indicate the presence of an asbestos fiber responsive to the electromagnetic field induced by electromagnets 72, 74 (see FIG. 6D). If not, second discriminator 108 determines that the fiber is not an asbestos fiber. Should second frequency and phase discriminator 108 determine that an asbestos fiber has been detected, a signal is transmitted directly to an "AND" gate 100 and the pulse amplitude corresponding to the magnetic field signal train M is transmitted to pulse amplitude comparator 104. Pulse amplitude comparator 104 determines whether the two corresponding pulse amplitudes received from pulse amplitude and area discriminator 102 and frequency phase and pulse shape discriminator 108 are equal. Where the pulse amplitudes are not equal, the asbestos monitor concludes that an asbestos fiber has not been detected. On the other hand, where the pulse amplitudes are equal pulse amplitude comparator 104 transmits a signal to "AND" gate 110. When "AND" gate 110 receives signals from both frequency phase and pulse discriminator 108 and pulse amplitude comparator 104, a signal is transmitted to an asbestos fiber counter 112 and the asbestos fiber is counted.

Zeroing and calibration steps are also contemplated and are preferably performed before and after each sampling session. During calibration and checking, solenoid valve 46 is closed so that all exhaust from main branch 40 is diverted to secondary exhaust branch 44 and into clean air pipes 54, 56. In this cycle of operation, flow tube 12, side duct 32 with filter 34 and vacuum 35, and secondary exhaust branch 44 including clean air pipes 54, 56 constitute a closed system and no air is drawn through inlet port 24. Clean, filtered air is blown through clean air pipes 54, 56, across the optical surfaces of beam expander 82 and external laser cavity mirror 90, through apertures 86, 88 and sensing flow tube 12 to side duct 32 and membrane filter 34. In this manner, the flow system is purged and the sensing system may be calibrated to zero prior to ambient atmosphere sampling. Pulsed light emitting diodes 94, 96 also provide a simulated fiber light stimulus beaming across each sensing stage for calibration. In this calibration procedure, the first substage LED 94 is activated to transmit a light pulse train burst having a pulse amplitude and area which simulate passage of a fiber of specific dimensions. After the expected time delay for a fiber to travel between sensing stages, the second LED 96 is activated to transmit a corresponding pulse train at second sensing stage detector 22 having amplitude and area representative of an asbestos particle. Preferably, the intensity of the LED light pulses is controlled by a detector that senses the helium-neon laser power, thereby normalizing the calibration check with respect to the fiber illumination intensity. Of course, it is contemplated that if a CCD array fiber detection configuration is used, a corresponding LED calibration array having an LED source corresponding to each CCD element should be used.

In a first alternative embodiment illustrated in FIGS. 8 and 9, it is contemplated that satisfactory results may be obtainable using only a time-varying magnetic field. In this embodiment, flow tube 12 is provided with only one sensing zone 116 having electromagnets 172, 174 which are driven with a time-varying electric field to produce a time-varying magnetic field. It is further contemplated that, in the absence of a constant alignment field, electromagnets 172, 174 might be phased so as to achieve continuous 360° rotation of fibers within the field. Of course, this may advantageously be accomplished using three electromagnets driven by sinusoidal voltages having 0°, 120° and 240° phase angles, respectively. In the first alternative embodiment, illumination and detection preferably are accomplished in the same manner as in the second stage of the preferred embodiment.

In a second alternative embodiment illustrated in FIGS. 10 and 11, a single sensing zone 216 is provided with a first set of electromagnets 265, 266, 268, 270 and a second set of electromagnets 272, 274. The first set of electromagnets is driven with a constant electric field to establish a constant magnetic field to align asbestos fibers. By way of example, a constant d.c. electric field might be applied across electromagnets 265, 270 and 266, 268, respectively, to produce a magnetic field which vertically aligns asbestos fibers in the sample. Half-wave sinusoidal voltages 90° out of phase are simultaneously applied to electromagnets 272, 274 in the manner previously described in connection with the preferred embodiment to create a time-varying magnetic field. The end result is that asbestos fibers aligned by the constant magnetic field induced by the first set of electromagnets oscillate in response to the time-varying magnetic field induced by the second set of electromagnets. In the second alternative embodiment, illumination and detection preferably are accomplished in the same manner as in the second stage of the preferred embodiment.

It will be readily apparent that the aerosol monitor according to the present invention is capable of distinguishing and counting asbestos fibers in order to accurately determine asbestos concentration on a real time basis. Surprisingly, this remarkable result is obtained in a compact, rugged and portable structure suitable for on-site use before, during and after asbestos removal operations. As further advantages of the invention, clean air flow across optical surfaces protects those surfaces from abrasive materials in the sample specimen and high intensity, bilateral illumination perpendicular to the fiber axes increases sensitivity to smaller fibers on the order of 0.5 micrometers in length and 0.1 micrometers in diameter.

To the extent not already indicated, it will be understood by those of ordinary skill in the art that any one of the various specific embodiments herein described and illustrated may be further modified to incorporate features shown in other of the specific embodiments. By way of example only, it is contemplated that the order of the electric and hybrid electric/magnetic fields in the detection sequence might be reversed, or under some circumstances use of only a hybrid electric/magnetic field may be adequate or desirable. Other variations will occur to those of ordinary skill in the art after practice with the invention.

The invention in its broader aspects therefore is not limited to the specific embodiments herein shown and described but departures may be made therefrom within the scope of the accompanying claims without departing from the principles of the invention and without sacrificing its chief advantages.

What is claimed is:

1. A real time asbestos aerosol monitor comprising:
sampling means for obtaining an ambient air sample and providing said sample to a sensing chamber having a sensing zone;
magnetic field means for creating a time-varying magnetic field at said sensing zone in order to cause airborne asbestos fibers in said sample to rotate;
illumination means for illuminating said fibers; and
a detector for detecting light scattered by said fibers to produce a scattered light signal indicative of the presence of an asbestos fiber.

2. The real time asbestos aerosol monitor according to claim 1 wherein said time-varying magnetic field is configured and dimensioned to cause asbestos fibers in said sample to rotate through an angle of at least 360°.

3. A real time asbestos aerosol monitor comprising:
sampling means for obtaining an ambient air sample and providing said sample to a sensing chamber having a sensing zone;
alignment field means for creating a constant alignment field at said sensing zone to align fibers in said sample at a first fiber angle;
magnetic field means for creating a time-varying magnetic field at said sensing zone, said time-varying magnetic field being disposed at an angle relative to said alignment field, said time-varying magnetic field causing asbestos fibers aligned at said first fiber angle to oscillate between said first fiber angle and a second fiber angle;
illumination means for illuminating said fibers aligned at said first fiber angle perpendicular to the axes of said fibers; and
a detector for detecting light scattered by said fibers oscillating between said first and second fiber angles to produce a detector signal, said detector signal indicating whether an asbestos fiber has been detected.

4. The real time asbestos aerosol monitor according to claim 3 wherein said constant alignment field is a magnetic field.

5. The real time asbestos aerosol monitor according to claim 3 wherein said constant alignment field is an electric field.

6. The real time asbestos aerosol monitor according to claim 3 wherein said illumination means further includes a an intracavity laser, laser beam expander and a first illumination aperture disposed at one end of said sensing chamber and a second illumination aperture and a plane mirror perpendicular to the laser beam at the opposite end of said sensing chamber.

7. The real time asbestos aerosol monitor according to claim 6 wherein said detector is disposed at substantially 90° to said illumination laser beam.

8. A real time asbestos aerosol monitor comprising:
sampling means for obtaining an ambient air sample and providing said sample to a sensing chamber having a first sensing zone and a second sensing zone;
first electric field means for creating a first constant electric field at said first sensing zone to align fibers in said sample at a first fiber angle;
second electric field means for creating a time-varying electric field at said first sensing zone, said time-varying electric field being at an angle relative to said first constant electric field, said time-varying electric field causing fibers aligned at said first fiber angle to oscillate between said first fiber angle and a second fiber angle;
third electric field means for creating a second constant electric field at said second sensing zone to align fibers in said sample at a third fiber angle;
magnetic field means for creating a time-varying magnetic field at said second sensing zone, said time-varying magnetic field being disposed at an angle relative to said second constant electric field, said time-varying magnetic field causing asbestos fibers aligned at said third fiber angle to oscillate between said third fiber angle and a fourth fiber angle;
illumination means for illuminating said fibers aligned at said first fiber angle in said first sensing zone and said third fiber angle in said second sensing zone perpendicular to the axes of said fibers;
a first sensing zone detector for detecting light scattered by said fibers oscillating between said first fiber angle and said second fiber angle to produce a first detector signal, said first detector signal indicating whether a fiber has been detected; and
a second sensing zone detector for detecting light scattered by said fibers oscillating between said third fiber angle and said fourth fiber angle to produce a second detector signal, said second detector signal indicating whether an asbestos fiber has been detected.

9. The real time asbestos aerosol monitor according to claim 8 wherein said sensing chamber further comprises a sensing tube.

10. The real time asbestos aerosol monitor according to claim 8 wherein said first fiber angle and said third fiber angle are substantially the same.

11. The real time asbestos aerosol monitor according to claim 8 further comprising means for determining from said first detector signal the length of a detected fiber.

12. The real time asbestos aerosol monitor according to claim 8 further comprising means for determining from said first detector signal the aspect ratio of a detected fiber.

13. The real time asbestos aerosol monitor according to claim 11 further comprising means for correlating said first detector signal and said second detector signal in order to determine the length of each detected asbestos fiber.

14. The real time asbestos aerosol monitor according to claim 9 wherein said sampling means further comprise an inlet port, an impaction separator, an electric charge neutralizer and a feed pipe for providing said sample to said sensing tube.

15. The real time asbestos aerosol monitor according to claim 14 further comprising a vacuum source connected to said sensing tube at the opposite side of said first and second sensing zones from said feed pipe.

16. The real time asbestos aerosol monitor according to claim 15 wherein said vacuum source further comprises an in-line filter connected to a pulsation dampener and an air pump.

17. The real time asbestos aerosol monitor according to claim 9 wherein said illumination means further comprise a laser disposed at one end of said sensing tube for transmitting a laser beam along the axis of the sensing tube.

18. The real time asbestos aerosol monitor according to claim 17 wherein said illumination means further includes an intracavity laser, laser beam expander and a first illumination aperture disposed at one end of said sensing tube and a second illumination aperture and a plane mirror perpendicular to the laser beam at the opposite end of the sensing tube.

19. The real time asbestos aerosol monitor according to claim 18 further including a polarizing filter and a field of view slit aperture disposed in the optical path of each of said first and second detectors.

20. The real time asbestos aerosol monitor according to claim 18 wherein said first and second sensing zone detectors are disposed at substantially 90° to said illumination laser beam.

21. The real time asbestos aerosol monitor according to claim 20 further comprising at least one calibration light source for illuminating each of said first and second detectors for calibration.

22. The real time asbestos aerosol monitor according to claim 20 wherein said first and second detectors are photomultipliers.

23. The real time asbestos aerosol monitor according to claim 20 wherein said first and second detectors are charge coupled devices.

24. A method of identifying on a real time basis asbestos fibers contained in an air sample comprising the steps of:
obtaining an ambient air sample;
passing said air sample through a sensing zone;
exposing said air sample in said sensing zone to a time-varying magnetic field in order to cause airborne asbestos fibers in said sample to rotate in response to said time-varying magnetic field;
illuminating said fibers;
detecting light scattered by said fibers to produce a scattered light signal; and
identifying from said scattered light signal asbestos fibers in said sample.

25. The method according to claim 24 wherein said time-varying magnetic field is configured and dimensioned to cause said asbestos fibers in said sample to rotate through an angle of at least 360°.

26. A method of identifying on a real time basis asbestos fibers contained in an air sample comprising the steps of:
obtaining an ambient air sample;
passing said air sample through a sensing zone;
simultaneously exposing said air sample in said sensing zone to a constant electric field to align all fibers in said sample at a first fiber angle, and a time-varying magnetic field disposed at an angle relative to said electric field, said time-varying magnetic field causing asbestos fibers in said sample to rotate between said first fiber angle and a second fiber angle;
illuminating said sample perpendicular to the axes of said fibers;
providing a detector for detecting light scattered by said fibers, said detector producing a scattered light signal;
determining from said scattered light signal whether a fiber has rotated in response to said time-varying magnetic field; and
counting as an asbestos fiber any fiber determined to have rotated in response to said magnetic field.

27. The method according to claim 26 wherein said detector is disposed at substantially a right angle to said illumination.

28. A method of identifying on a real time basis asbestos fibers contained in an air sample comprising the steps of:
obtaining an ambient air sample;
passing said air sample through a first sensing zone;
simultaneously exposing said sample in said first sensing zone to a first constant electric field to align all fibers contained in said air sample at a first fiber angle, and a time-varying electric field at an angle to said first constant electric field to periodically oscillate said aligned fibers between said first angle and a second fiber angle;
illuminating said sample in said first sensing zone perpendicular to the axes of said fibers;
providing a first sensing zone detector for detecting light scattered by said fibers in said first sensing zone, said first sensing zone detector producing a first scattered light signal;
determining from said first scattered light signal whether a fiber has been detected at said first sensing zone;
passing said air sample through a second sensing zone;
simultaneously exposing said sample in said second sensing zone to a second constant electric field to align all fibers contained in said air sample at a third fiber angle, and a time-varying electromagnetic field at an angle to said second constant electric field to periodically oscillate asbestos fibers from said third fiber angle to a fourth fiber angle;

illuminating said sample in said second sensing zone perpendicular to the axes of said fibers;

providing a second sensing zone detector for detecting light scattered by said fibers in said second sensing zone, said second sensing zone detector producing a second scattered light signal; and determining from said second scattered light signal whether an asbestos fiber has been detected at said second sensing zone.

29. The method according to claim 28 wherein said first sensing zone detector is disposed at substantially a right angle to said first sensing zone illumination.

30. The method according to claim 28 further comprising the step of determining from said first scattered light signal the length of the aligned, periodically oscillated fibers.

31. The method according to claim 28 further comprising the step of determining from said first scattered light signal the aspect ratio of the aligned, periodically oscillated fibers.

32. The method according to claim 28 wherein said first fiber angle is substantially equal to said third fiber angle.

33. The method according to claim 28 wherein said second sensing zone detector is disposed at substantially a right angle to said second sensing zone illumination.

34. The method according to claim 28 further comprising the steps of:

correlating the first scattered light signal with the second scattered light signal corresponding to the same sample portion;

counting asbestos fibers in a sample within a predetermined size range.

* * * * *

UNITED STATES PATENT AND TRADEMARK OFFICE
CERTIFICATE OF CORRECTION

PATENT NO. : 4,940,327

DATED : July 10, 1990

INVENTOR(S) : Pedro Lilienfeld

It is certified that error appears in the above-identified patent and that said Letters Patent is hereby corrected as shown below:

Column 5, line 32, "stages As" should read --stages.  As--

Column 8, line 27, "response As" should read --response.  As--

Signed and Sealed this

Twelfth Day of January, 1993

Attest:

DOUGLAS B. COMER

*Attesting Officer*  *Acting Commissioner of Patents and Trademarks*